United States Patent [19]

Chamberlin et al.

[11] 4,331,785
[45] May 25, 1982

[54] VINYL SUBSTITUTED CYCLIC POLYETHERS AND ADDITION POLYMERS THEREOF

[75] Inventors: Thomas A. Chamberlin; Donald A. Tomalia, both of Midland, Mich.

[73] Assignee: The Dow Chemical Co., Midland, Mich.

[21] Appl. No.: 107,813

[22] Filed: Dec. 28, 1979

Related U.S. Application Data

[60] Division of Ser. No. 961,159, Nov. 16, 1978, Pat. No. 4,256,855, which is a division of Ser. No. 751,870, Dec. 17, 1976, Pat. No. 4,139,539, which is a continuation-in-part of Ser. No. 517,703, Oct. 24, 1974, abandoned.

[51] Int. Cl.³ .......................... C08F 8/42; C08K 3/10
[52] U.S. Cl. .................................. 525/367; 210/732; 210/733; 423/181; 521/31; 525/326; 525/329; 526/266; 526/270
[58] Field of Search ............... 210/732, 733; 423/155, 423/178, 179, 181; 525/367; 521/31

[56] References Cited
U.S. PATENT DOCUMENTS 3,515,707  6/1970  Reimschuessel et al. .......... 525/367
4,110,520  8/1978  Miyajima ............................ 525/367

Primary Examiner—Harry Wong, Jr.
Attorney, Agent, or Firm—David H. Fifield; Douglas N. Deline

[57] ABSTRACT

Compounds represented by the formula

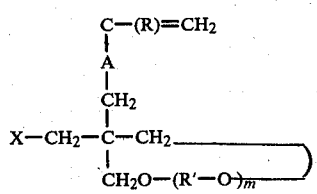

and addition polymers thereof where m is an integer from 2 to about 10, X- is chlorine, hydroxy, carboxy or

-AC(R)=CH$_2$

-R is hydrogen or methyl, -R' is an ethylene or propylene group and

-AC(R)=CH$_2$ is one of

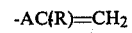

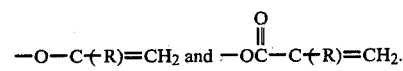

These compounds and their addition polymers form complexes with alkali metal or alkaline earth metal salts and permit the concentration of aqueous solutions of said salts. For example, a compound of the formula

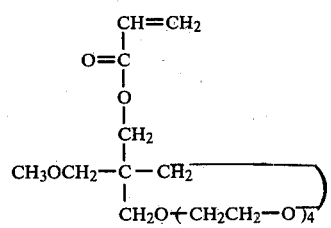

is polymerized with an azobis(isobutyronitrile) catalyst to form addition polymers of the repeating unit

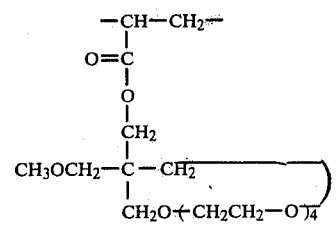

When cross-linked, rendering it water-insoluble, such an addition polymer concentrates an aqueous solution of sodium chloride when contacted with same at about 0° C.

2 Claims, No Drawings

VINYL SUBSTITUTED CYCLIC POLYETHERS AND ADDITION POLYMERS THEREOF

CROSS-REFERENCE TO RELATED APPLICATIONS

This is a division of pending application Ser. No. 961,159, filed Nov. 16, 1978, now U.S. Pat. No. 4,256,855, which is a division of copending application Ser. No. 751,870, filed Dec. 17, 1976, now U.S. Pat. No. 4,139,539, which is a continuation-in-part of our copending application Ser. No. 517,703, filed Oct. 24, 1974, now abandoned.

Precursors of the compounds claimed herein are disclosed in the application of Steiner, Ser. No. 902,204, filed May 2, 1978, now U.S. Pat. No. 4,183,862, and the copending application of Steiner et al., Ser. No. 055,874, filed July 6, 1979.

BACKGROUND OF THE INVENTION

Novel compounds of the invention belong to a class of cyclic polyethers comprising one or more vinylic functional groups attached to a tertiary carbon of the polyether ring through an ester or an ether linkage. The novel addition polymers prepared therefrom comprise a polyethylene backbone with pendent cyclic polyether groups attached thereto.

Polymers of the repeating unit

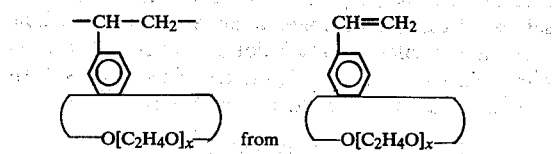

where x is 4 and 5 are described by Kopolow et al. in *Macromolecules* 4:359 (1971).

Polymers of the repeating unit

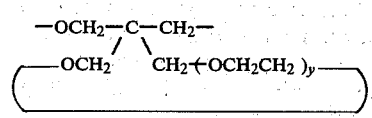

where y is 3 to about 10 are described in U.S. Pat. No. 3,763,188 to Krespan and are prepared from oxetane functional macrocycles. Krespan describes dihydroxymethyl precursors of the instant invention in U.S. Pat. No. 3,860,611.

Compounds with polyoxyalkylene cyclomers have been shown to form complexes with certain alkali metal and alkaline earth metal cations in U.S. Pat. Nos. 3,562,295 and 3,686,225.

SUMMARY OF THE INVENTION

The invention consists of novel compounds represented by the formula:

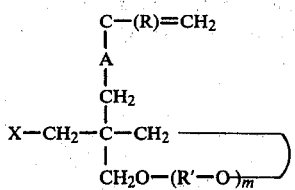

and addition polymers thereof wherein m is an integer from 2 to about 10; —X is chlorine, carboxy, hydroxy or

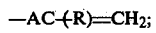

—R is hydrogen or methyl; —R′— is ethylene, 1,2-propylene or 1,3-propylene; and

—AC($R$)=CH$_2$ is one of

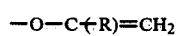

and

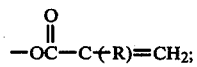

provided that when X is chlorine,

The invention also concerns a process for concentrating aqueous solutions of alkali metal or alkaline earth metal salts comprising contacting a cross-linked, water-insoluble polymer of the invention with said aqueous salt solution.

Preferred embodiments of the invention are those wherein —R′— is ethylene and those wherein m is 3 to about 7. Further preferred are embodiments wherein X is chlorine, wherein X is methoxyl, wherein X is hydroxyl, or wherein X is —AC($R$)=CH$_2$, —AC($R$)=CH$_2$ being the same moiety in both positions.

DETAILED DESCRIPTION OF THE INVENTION

Monomers

The vinyl monomers of (I) wherein X is chlorine are prepared by contacting a compound of the formula:

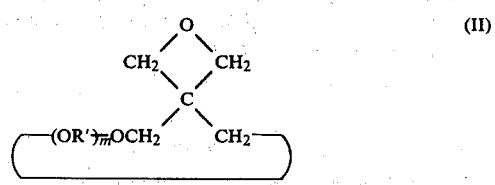

(II)

with acryloyl or methacryloyl chloride. Compounds of formula (II) are prepared by contacting an alkali metal salt of a polyalkylene glycol of the formula M($OR'$)$_m$OM (III)

wherein M is an alkali metal such as sodium or potassium and m is an integer from 2 to about 10, with a 3,3-bis(halomethyl) oxetane for example, a compound of the formula

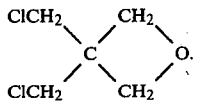 (IV)

Reactants (III) and (IV) are contacted in about equal molar proportions under an inert atmosphere conveniently at temperatures from about 0° to about 100° C. The product of this reaction will be comprised of (II) and congeners thereof with more than one oxetane functionality. Compound (II) may be separated from these congeners by suitable means such as fractional distillation or gel permeation chromatography or the congeneric mixture may be used in preparing congeners of (I) with multiple tertiary carbons attached to vinyl functional groups, which congeners may likewise be addition polymerized to form crosslinked ethylene polymers.

Compounds of formula (II), when contacted with an acid of the formula

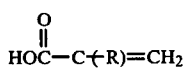

form compounds of formula (I) where X is hydroxyl and

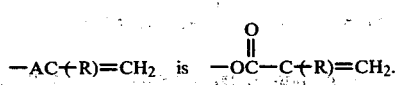

Compounds of formula (II) may also be contacted under acid conditions with a compound of the formula R″—OH where R″ is hydrogen or a straight chain or branched lower hydrocarbyl moiety comprising from 1 to about 10 carbon atoms. Such a reaction produces a product of the formula

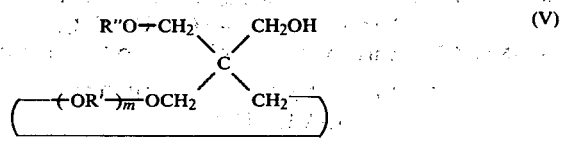 (V)

In preferred embodiments of the invention, R″ is hydrogen or a methyl group. Compound (V) may then be contacted with acrylic or methacrylic acid or acid chloride in the presence of a tertiary amine, i.e. pyridine, triethylamine, etc. to give monofunctional materials of (I) represented by the formula

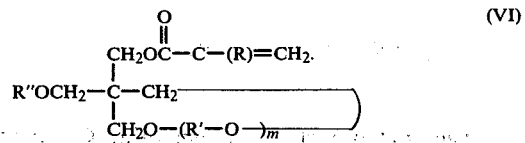 (VI)

Compounds of formula (V) may be contacted with about an equal molar amount of a vinyl ether of the formula

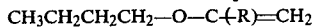

in the presence of a mercuric acetate catalyst to give compounds of the formula

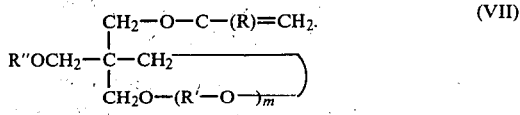 (VII)

(VII).

Analogs of compounds (VI) and (VII), respectively, wherein R″ is hydrogen may be produced by contacting a compound of formula (V), wherein R″ is hydrogen (prepared from (II) and dilute aqueous acid solution), with equal molar quantities of each of these two types of acrylic functional materials, respectively, in the manner described above. When the molar ratio of the acrylic functional reactant to the diol of (V) is allowed to exceed unity, compounds of formula (I) wherein X is

will be formed in proportionately increasing quantities. Employment of excess acrylic reactant (i.e., in more than twice the molar quantity of (V) diol) will result in symmetric acrylic difunctional products of formula (I) wherein X is —AC(—R)═CH₂ and —AC(—R)═CH₂ is the same in both positions.

In the preparation of the foregoing monomers, the reactions will be carried out at moderate temperatures to avoid premature polymerization. In some instances the addition of inhibitors such as phenothiazine, hydroquinone, diphenyl picrylhydrazyl and the like may be beneficial. The monomers, while they may be polymerized to form the polymers described below, may themselves be used to complex alkaline metal and alkaline earth metal salts from solutions. The complexes may thereafter be broken, by the choice of a suitable solvent, to recover salts in pure form.

Polymers

The invention polymers are prepared from the respective monomers using standard addition polymerization techniques commonly employed for acrylic, vinyl, and other ethylenic functional monomers. In some instances, all that will be required is the application of heat. The use of standard addition polymerization catalysts and initiators, such as trialkyl aluminums, alkyl aluminum halides, potassium persulfate, azobis(isobutyronitrile) (AIBN), peroxides and the like, may be beneficially employed.

The polymers may be homopolymers of the monomers described above or the monomers may be copolymerized with comonomers of ethylene functionality; for example, with acrylamide, methacrylamide, vinyl chloride, vinylidene chloride, styrene, vinyl toluene, maleic anhydride and the like. The monomers may be copolymerized with materials of multiple vinyl functionality such as methylene bis(acrylamide), ethylene glycol dimethacrylate, trimethylolpropane trimethacrylate, tetraethylene glycol dimethacrylate and the like, to form highly cross-linked polymers. The difunctional monomers of the invention also will produce cross-linked polymers. The degree of cross-linking may be readily controlled by adjusting the amount of multiple vinyl-functional materials, as is well known in the art.

The invention polymers with pendant macrocycles may be used to extract or concentrate alkali metal and alkaline earth metal salts of aqueous solutions and to absorb acid gases such as sulfur dioxide from gas streams. They also imbibe water strongly when crosslinked and as such are useful absorbent materials.

Preferred embodiments of the invention include those polymers wherein —R'— is an ethylene unit and those wherein m is an integer from 3 to about 7.

SPECIFIC EMBODIMENTS OF THE INVENTION

EXAMPLE 1

Precursors

A compound of formula (II), wherein R' was ethylene and m was 4, was prepared by contacting 3,3-bis(-chloromethyl) oxetane with the disodium salt of tetraethylene glycol in about equal molar quantities. The two reactants were dissolved in t-butanol solvent and contacted under a nitrogen atmosphere in a flask equipped with mechanical stirring and a condenser. The solution was heated to reflux temperature and maintained for about two hours at about 85° C. pot temperature. Heating was discontinued and the mixture was vacuum filtered while still warm to remove the sodium chloride precipitate which had formed. Evaporation of the filtrate yielded a clear, yellowish oil which was purified by fractional distillation to give the oxetane functional cyclic polyether:

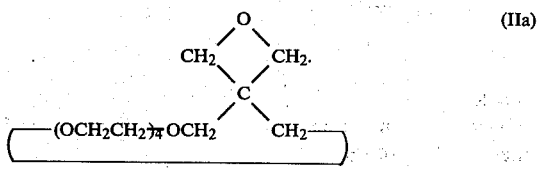

The oxetane (IIa) (0.1 mol), 50 milliliters of water and 9 milliliters of 30% aqueous hydrogen peroxide were stirred and heated to about 50° for 20 hours then refluxed for three hours. Excess water was removed on a rotary evaporator to give a liquid product. This product was distilled and the material that came over at about 210° C. under vacuum at 0.4 millimeter pressure was shown by infrared (IR) and nuclear magnetic resonance (NMR) spectroscopy to be the compound of the formula

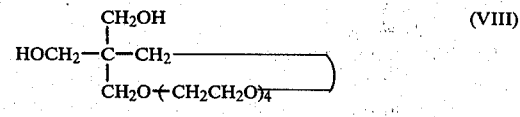

The compound of formula (VI) wherein —R'— was ethylene, m was 4 and R" was methyl, was prepared by refluxing the oxetane (II) of appropriate m and R' in excess methanol with a trace of sulfuric acid. The reaction mixture was then distilled at 129° to 133° C. under vacuum at 0.02 millimeter of pressure to obtain the desired product of the formula

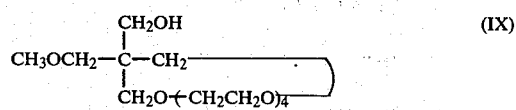

EXAMPLE 2

Oxetane-Methacryloyl Chloride Adduct and Homopolymers 7.3 Grams of the oxetane produced above of formula (IIa) was mixed neat with 3.8 grams of methacryloyl chloride and heated under nitrogen at reflux for about two hours. The product was shown by NMR analysis to be the compound of the formula

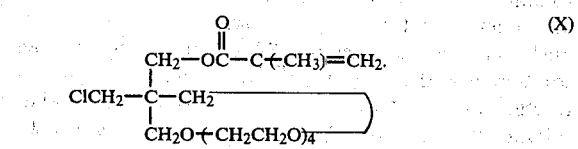

In 50 milliliters of dry tetrahydrofuran (THF) were dissolved 5 grams of the methacrylate of formula (X) and to this was added 0.05 gram of azobis(isobutyronitrile) (hereafter AIBN). The mixture was refluxed under nitrogen for about 16 hours, allowed to cool and the solvent removed by evaporation to give a tacky yellow material which redissolved in THF. 4.1 Grams of this polymeric product in 20 milliliters of THF was then contacted with 2.4 grams of sodium sulfide hydrate (9H$_2$O) and the mixture was refluxed for two hours. A brown suspension formed, the mixture was allowed to cool and was evaporated on a rotary evaporator to give a tan, solid product.

EXAMPLE 3

Dimethacrylate Cyclic Polyether

A compound of the formula

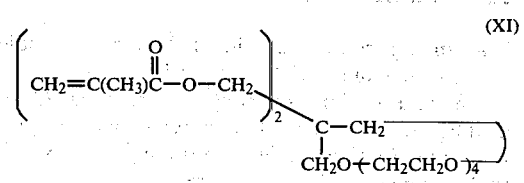

was prepared from the diol (VIII) and methacryloyl chloride by contacting methacryloyl chloride with the diol in a 2:1 mole ratio.

In 30 milliliters of benzene, 26.8 grams of the diol and 20.3 grams triethylamine were dissolved. To this was added dropwise a solution of 19.06 grams of methacryloyl chloride in 40 milliliters of benzene, with 0.04 gram of phenothiazine added to inhibit possible radical polymerization. As soon as the addition was started, a white precipitate began to form. Upon further addition of methacryloyl chloride, an exothermic reaction took place which was kept at a moderate temperature by slow addition of the methacryloyl chloride. The temperature reached about a 50° C. maximum. The addition was completed in about a one hour period and the mixture was stirred for another 4 hours at about 30° C. The material was then cooled in an ice bath and suction filtered to recover the liquid phase. This liquid filtrate was subjected to evaporation on a rotary evaporator for 10 to 20 minutes at 60° C. to remove benzene and other volatiles. 40 Grams of brownish-yellow liquid product were recovered, the theoretical yield for the diester being 39.2 grams. This liquid was dissolved in methylene chloride and passed through a short column of neutral alumina, eluting with methylene chloride and evaporating the excess eluent. Infrared and NMR analysis of the product showed it to be the diester of formula (XI).

EXAMPLE 4
Monofunctional Methacrylate

A mixture containing 10 grams of the compound (IX), 80 milliliters of toluene, 25 grams of anhydrous sodium carbonate, 0.5 gram of hydroquinone and 10 milliliters of methacryloyl chloride was stirred vigorously and heated at about 90° C. for 15 hours. The solution was then cooled, filtered and the filtrate extracted several times with toluene. Toluene and other solvents were removed from the extracted filtrate at 60° C. under vacuum at 15 millimeters of pressure to yield 12.7 grams of an oil which had a refractive index of 1.4824 (sodium D line at 25° C.). Vapor phase chromatographic analysis showed 83% conversion to product. This was the monofunctional methacrylate of the formula

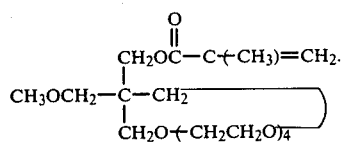
(XII)

Elemental analysis confirmed the structure.

| Calculated | Analysis |
|---|---|
| % C = 57.44 | 58.0, 58.3 |
| % H = 8.56 | 8.43, 8.35 |

A small portion of the liquid product was subjected to high vacuum distillation (at 0.05 millimeter pressure) but polymerization occurred at about 100° C. before distillation took place. This polymer was insoluble in methanol, THF, methylene chloride, and in N,N-dimethylformamide (DMF).

The liquid product itself polymerized on standing for about two days at ambient temperature. This polymerization was brought to completion by heating at 80° C. for about 12 hours under vacuum at 12 millimeters of pressure. The resulting product was a hard transparent polymer.

EXAMPLE 5
Monofunctional Acrylate

A solution containing 15.2 grams of compound (IX), 6 grams triethylamine, and 0.05 gram of 2,2-diphenyl-1-picrylhydrazyl dissolved in 250 milliliters of ethyl ether, was stirred at room temperature while a solution of 6 grams acryloyl chloride dissolved in 50 milliliters of ethyl ether was added dropwise to the mixture. The resultant two-phase solid-liquid system was stirred for about 12 hours and analyzed by vapor phase chromatography, which showed that no starting material remained. The mixture was filtered and the liquid filtrate subjected to 50° C. under vacuum at 0.05 millimeter of pressure to remove solvents giving 11.4 grams of a red, oily liquid. The solids were dissolved in water and then extracted with two 100 milliliter portions of methylene chloride. This organic phase was dried with magnesium sulfate and volatiles were removed as before to give 4.0 grams more of the red oil, a compound of the formula

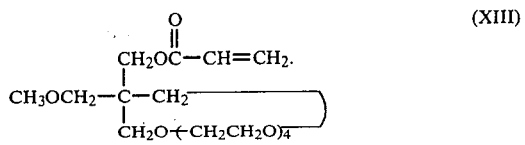
(XIII)

This product was found to be soluble in hexane, cyclohexane, carbon tetrachloride, water saturated ammonium chloride, nitrobenzene and isopropanol.

EXAMPLE 6
Monofunctional Vinyl Ether

A mixture containing 15.4 grams of the compound (IX), 25 milliliters of n-butyl vinyl ether and 0.5 gram of mercuric acetate was stirred and heated at about 50° C. for 20 hours. Solvents were removed from the product by heating at about 80° C. under 20 millimeters of pressure, absolute, to give 16.9 grams of an oily material which was then vacuum distilled at 0.1 millimeter of pressure. The material which distilled between 153° and 156° C. was found to have a refractive index of approximately 1.4740 (sodium D line at 25° C.). Vapor phase chromatographic analysis of the material showed about 55% conversion to the compound of the formula

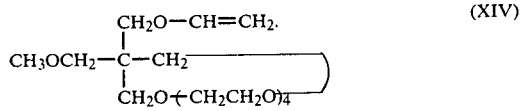
(XIV)

NMR analysis confirmed the structure. (Pressures, where mentioned above, are absolute pressures in millimeters of mercury).

EXAMPLE 7
Copolymers of the Monoacrylate

In the following examples, the compound (XIII) prepared above was copolymerized with different comonomers to produce crosslinked polymers. In the first instance, ampoules loaded with 1 gram of the cyclic ether monoacrylate, (XIII), 0.5 gram of a benzene solution of benzoyl peroxide having 0.0102 gram benzoyl peroxide per gram of solution, 2.5 grams of hexane and varying amounts of stock Solution A were pretreated and then polymerized. Stock Solution A was a benzene solution with 0.0764 gram ethylene glycol dimethacrylate (EGDMA) per gram of solution. Pretreatment consisted of shaking the solutions vigorously with 2.0 grams of alumina (Woelm, acidic activity grade 1), filtering through glass wool, deoxygenating by passing helium through the solution, freezing with a dry ice-methylene chloride mixture and then flame sealing the ampoules. After warming to room temperature, the ampoules were thoroughly mixed by shaking and then were heated for approximately 12 hours at 100° C. The ampoules were cooled and opened and the polymers were isolated by treatment with methanol and ethyl ether. The results are shown in the following table.

TABLE 1

| Run # | Solution A (grams) | EGDMA (mole %) | Product |
|---|---|---|---|
| 1 | 0.1 | 1.4 | Polymer |

TABLE 1-continued

| Run # | Solution A (grams) | EGDMA (mole %) | Product |
|---|---|---|---|
| | | | soluble in MeOH |
| 2 | 0.2 | 2.8 | Polymer soluble in MeOH |
| 3 | 0.5 | 7.0 | 0.12 g polymer insoluble in MeOH |
| 4* | 0.5 | 7.0 | Polymer soluble in MeOH |
| 5 | 1.0 | 14.0 | Polymer soluble in MeOH |

*pretreated with 2.0 g basic alumina instead of acidic alumina

In the following runs, glass ampoules were loaded with 1.0 gram of (XIII), 2.5 grams of deionized water, 0.5 gram of a 5 weight percent aqueous potassium persulfate solution, and varying amounts of a stock Solution B which was methylene bis(acrylamide) (MBA) in methanol, 0.06 gram MBA per gram solution. The solutions were deoxygenated with helium, frozen and flame sealed in the ampoules. After warming to room temperature, they were thoroughly mixed and heated at about 80° C. for approximately 12 hours. After cooling, the ampoules were opened and the polymers isolated by precipitation in methanol followed by several ethyl ether washings. Solvent was removed by vacuum drying. The results are shown in the following Table 2.

TABLE 2

| Run # | Solution B (grams) | MBA (mole %) | Product (grams) | Reactants going to Polymers (wt. %) |
|---|---|---|---|---|
| 6 | 0.1 | 1.4 | 0.604 | 60.8 |
| 7 | 0.2 | 2.8 | 0.649 | 65.3 |
| 8 | 0.5 | 7.1 | 0.885 | 86.1 |
| 9 | 1.0 | 14.1 | 0.889 | 89.5 |
| 10 | 2.0 | 28.2 | 0.848 | 85.4 |

EXAMPLE 8

Polymerization of Cyclic Polyether Monomethacrylate with Various Cross-linking Comonomers In the following experiments, the monomethacrylate (XII) was copolymerized with various polyfunctional comonomers in a manner similar to that of Example 7. Solutions were prepared containing 1 gram of the compound (XII), 0.5 gram of the benzene solution containing 0.00142 gram of AIBN per gram solution, varied amounts of stock solutions of the comonomers and enough benzene to bring the total to 4.0 grams. The resulting solutions were treated with 2.0 grams of acidic alumina, as above, filtered through glass wool into ampoules, deoxygenated with helium, frozen and the ampoules flame sealed. After warming to room temperature, the contents were thoroughly mixed and then heated to about 80° C. for approximately 12 hours. The ampoules were cooled, opened and the contents treated with methanol, ethyl ether and then vacuum dried to give the polymeric products.

In Runs 11–16, the stock solutions are benzene solutions of the following make-up:

Solution C: 0.1075 gram of EGDMA/gram solution;

Solution D: 0.176 gram of trimethylolpropane trimethacrylate (TPTMA)/gram solution; and Solution E: 0.180 gram of tetraethylene glycol dimethacrylate (TeGDMA)/gram solution.

The results are described in Table 3, below.

TABLE 3

| Run # | Cross-Linker Solution (grams) | Mole % of Cross-Linker | Product (gram) | Reactants going to Polymers (wt. %) |
|---|---|---|---|---|
| 11 | 0.10 Sol'n. C | 2.0 EGDMA | 0.333 | 33.5 |
| 12 | 0.25 Sol'n. C | 5.0 EGDMA | 0.348 | 35.0 |
| 13 | 0.50 Sol'n. C | 10.2 EGDMA | 0.414 | 41.6 |
| 14 | 1.00 Sol'n. C | 20.4 EGDMA | 0.254 | 25.5 |
| 15 | 0.50 Sol'n. D | 10.2 TPTMA | 0.696 | 70.0 |
| 16 | 0.50 Sol'n. E | 10.2 TeGDMA | 0.630 | 63.3 |

EXAMPLE 9

Sodium Chloride Concentration by Polymers

The polymers prepared in Examples 7 and 8, above, were ground then contacted with aqueous sodium chloride solutions of known concentration. The polymer samples ranged from about 0.2 gram to about 0.8 gram in size. The polymers of Example 7, derived from the monoacrylate (VIII), were contacted with, 10 milliliters of NaCl solution, containing 1.028 milliequivalents (meq) of the salt. The system was allowed to equilibrate at 0° C. for about one week. At the end of that time, the polymer-solution mix was centrifuged in a laboratory centrifuge at about 5000 rpm and the supernate was withdrawn. The supernate was weighed and the chloride meq thereof determined by Vollhard titration.

The polymers of Example 8 were similarly prepared, contacted with 5 milliliters of an aqueous NaCl standard, equilibrated for about one week at 0° C., the supernate separated and titrated for chloride meq. The same polymers were then contacted, overnight, with the same standard solution at ambient temperature (about 20° C.), supernate separated and titrated for chloride (polymers 14 and 15 with 1–2 ml standard samples).

The chloride meq of the polymer phase and the ml of aqueous solution sorbed by the polymer were calculated from the difference between these parameters in the NaCl standard and in the supernate. From this data, concentration of chloride ion in the polymer per ml of sorbed aqueous solution was calculated. The molar distribution coefficient, hereinafter $K_m$, was then calculated according to the following equation:

$$K_m = \frac{\text{meq Cl}^-/\text{ml aqueous solution sorbed in polymer}}{\text{meq Cl}^-/\text{ml supernate}}$$

The molar distribution constants for the various polymers at 0° and 20° C. are shown in Table 4, below. It may be observed that where $K_m$ is greater than unity, a preferential concentration of the salt solution in the polymer occurred. The data indicates that such a preferential concentration occurs at 0° C. The comparative runs with the more highly cross-linked polymers (#14 and 15) show that the concentrating effect reverses at the higher temperature. The preferential concentration of a salt in the polymer phase may be used to reduce the concentration of the salt in an aqueous solution that is contacted with the polymer in the manner described above. Under the conditions where $K_m$ is less than unity, a concentrating effect is observed in the supernate. Thermal reversibility permits "regeneration" of the polymer's activity by heating, as by contacting the polymer with a solution of hot water. Since the polymer may be immobilized in beds or columns in the manner of conventional ion exchange resins, these useful effects can be magnified by sequentially contacting an aqueous salt solution with a plurality of such polymer packed beds or columns.

TABLE 4

| Polymer No. | Km at 0° C. | at 20° C. |
|---|---|---|
| 5 | 1.52 | —# |
| 7 | 1.56 | —# |
| 8 | —* | —# |
| 9 | —* | —# |
| 10 | 1.25 | —# |
| 11 | polymer dissolved | 2.88 |
| 12 | —* | 1.14 |
| 13 | —* | 1.00 |
| 14 | 1.46 | 1.42 |
| 15 | 1.10 | 0.68 |
| 16 | —* | 1.04 | not run at 20° C.

*at 0° C., polymer completely swollen, supernate could not be separated from the swollen polymer.

We claim:

1. A process for concentrating an alkali metal or alkaline earth metal salt in aqueous solution comprising contacting an aqueous solution comprising said alkali metal or alkaline earth metal salt with a cross-linked, water-insoluble addition polymer of a compound represented by the formula

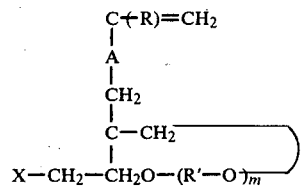

wherein m is an integer from 2 to about 10, —X is —Cl, —OR" or —AC—(R)=CH$_2$; —R is hydrogen or methyl; —R'— is ethylene, 1,2-propylene or 1,3-propylene; —R" is hydrogen or lower hydrocarbyl; and —A-C—(R)=CH$_2$ is selected from the group consisting of —O—C—(R)=CH$_2$ and

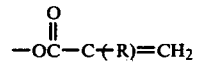

provided that when —X is —Cl, —AC—R)=CH$_2$ is

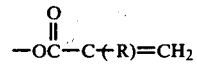

and further characterized in that when the cross-linked water-insoluble addition polymer is a homopolymer of the compound or a copolymer of the compound with a comonomer of monoethylene functionality, then —X is —AC—R)=CH$_2$; and when the cross-linked, water-insoluble addition polymer is a copolymer of the compound with a comonomer of multiple ethylene functionality then —X is —Cl, —OR" or —AC—R)=CH$_2$.

2. The process of claim 1 wherein in the addition polymer, X is methoxyl, —R' is ethylene, —A-C—R)=CH$_2$ is

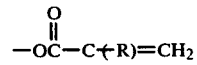

and m is 4 and said aqueous solution comprises sodium chloride.

* * * * *

UNITED STATES PATENT AND TRADEMARK OFFICE
CERTIFICATE OF CORRECTION

PATENT NO. : 4,331,785

DATED : May 25, 1982

INVENTOR(S) : Thomas A. Chamberlin and Donald A. Tomalia

It is certified that error appears in the above—identified patent and that said Letters Patent is hereby corrected as shown below:

Title page, Column 2, line 1, " -R' " should read -- -R'- --.

Column 4, line 10, "(VII)" should be deleted.

Column 9, Table 2, Run #8 under Product (grams), "0.885" should read -- 0.855 --.

Column 10, Table 3, Run #12 under Mole % of Crosslinker, "5.0 EGDMA" should read -- 5.1 EGDMA --.

Column 11, Table 4, under Polymer No., "5" should read -- 6 --.

Column 12, line 21, that portion of the formula reading "-AC-R)" should read -- -AC-(R) --.

Column 12, line 31, that portion of the formula reading "-AC-R)" should read -- -AC-(R) --.

Column 12, line 34, that portion of the formula reading "-AC-R)" should read -- -AC-(R) --.

Column 12, line 36, that portion of the formula reading "-R' " should read -- -R'- --.

UNITED STATES PATENT AND TRADEMARK OFFICE
CERTIFICATE OF CORRECTION

PATENT NO. : 4,331,785

DATED : May 25, 1982

INVENTOR(S) : Thomas A. Chamberlin and Donald A. Tomalia

It is certified that error appears in the above—identified patent and that said Letters Patent is hereby corrected as shown below:

Column 12, line 37, that portion of the formula reading "C-R)" should read -- C-(R) --.

Signed and Sealed this

Twenty-fifth Day of January 1983

[SEAL]

Attest:

GERALD J. MOSSINGHOFF

Attesting Officer

Commissioner of Patents and Trademarks